United States Patent
Powell et al.

(10) Patent No.: US 11,931,360 B2
(45) Date of Patent: Mar. 19, 2024

(54) COMPOSITIONS AND METHODS RELATING TO INHIBITORS OF PRO-INFLAMMATORY FACTORS FOR TREATMENT OF CANCER

(71) Applicant: Wayne State University, Detroit, MI (US)

(72) Inventors: Isaac J. Powell, Detroit, MI (US); Navnath S. Gavande, Rochester Hills, MI (US)

(73) Assignee: Wayne State University, Detroit, MI (US)

( * ) Notice: Subject to any disclaimer, the term of this patent is extended or adjusted under 35 U.S.C. 154(b) by 0 days.

(21) Appl. No.: 17/847,935

(22) Filed: Jun. 23, 2022

(65) Prior Publication Data
US 2023/0018174 A1    Jan. 19, 2023

Related U.S. Application Data (60) Provisional application No. 63/213,871, filed on Jun. 23, 2021.

(51) Int. Cl.
*A61K 31/506*    (2006.01)
*A61K 45/06*    (2006.01)
*C07D 401/14*    (2006.01)

(52) U.S. Cl.
CPC ............ *A61K 31/506* (2013.01); *A61K 45/06* (2013.01); *C07D 401/14* (2013.01)

(58) Field of Classification Search
CPC .. A61K 31/506; A61K 31/496; C07D 401/14; C07D 401/12
See application file for complete search history.

(56) References Cited

U.S. PATENT DOCUMENTS 6,174,887 B1 *    1/2001    Haruta .................. C07C 237/22
                                                                    514/331

FOREIGN PATENT DOCUMENTS

WO        WO-03055876 A1 *    7/2003    ........... A61K 31/415

OTHER PUBLICATIONS

Castration-mediated IL-8 Promotes Myeloid Infiltration and Prostate Cancer Progression bioRxiv preprint doi: https://doi.org/10.1101/651083; posted May 28, 2019 (Year: 2019).*
A review on pharmacophoric designs of antiproliferative agents Med Chem Res 2015, 24, 903-920 (Year: 2015).*
V. R. Solomon et.al. 18, Bioorg. Med. Chem. 1563-1572 (2010) (Year: 2010).*
C. L. Gladson et.al. 7(11) Cancer Biol Ther. 1849-1851 (2008) (Year: 2008).*
Z. A. Lopez-Bujanda et.al 2(8), Nat Cancer. 803-818 (2021) (Year: 2021).*
Kakutani, M. et al., JTE-607, a novel inflammatory cytokine synthesis inhibitor without immunosuppression, protects from endotoxin shock in mice, Inflammation Research, 48(8):461-468, 1999.

* cited by examiner

*Primary Examiner* — Brandon J Fetterolf
*Assistant Examiner* — Frank S. Hou
(74) *Attorney, Agent, or Firm* — Julie K. Staple; Dinsmore & Shohl LLP (57) ABSTRACT

Compositions and methods for treatment of cancer according to aspects of the present disclosure comprise compounds comprising or consisting of: structural formula (I) or (II) disclosed herein, or a salt, isomer, or derivative thereof.

20 Claims, 2 Drawing Sheets

COMPOSITIONS AND METHODS RELATING TO INHIBITORS OF PRO-INFLAMMATORY FACTORS FOR TREATMENT OF CANCER

REFERENCE TO RELATED APPLICATION

This application claims priority to U.S. Provisional patent Application Ser. No. 63/213,871, filed Jun. 23, 2021, the entire content of which is incorporated herein by reference.

FIELD OF THE INVENTION

This disclosure relates generally to compositions and methods for inhibiting pro-inflammatory factors, including cytokines and chemokines, receptors thereof, and stimulators thereof. According to specific aspects, this disclosure relates to compositions and methods for inhibiting pro-inflammatory factors including cytokines and chemokines, receptors thereof, and stimulators thereof, for treatment of cancer.

BACKGROUND OF THE INVENTION

Despite recent advances in cancer therapeutics, there is a continuing need for compositions and methods for treatment of cancer.

SUMMARY OF THE INVENTION

Compounds according to aspects of the present disclosure include, or consist of, structural formula (I):

where X is O, NH, or S; where $R_1$, $R_2$, and $R_3$, are each independently selected from the group consisting of H, Br, F, methyl, Cl, OH, CN, $NH_2$, and $CF_3$; where $R_4$ is H, C1-C6 unsubstituted or substituted, alkyl, cycloalkyl, aryl, phenyl, heteroalkyl, heterocycloalkyl, or heteroaryl; where $R_5$ is COOH, $CO_2R$, $SO_3H$, $SO_2NH_2$, $PO_3H$, $CONH_2$, CONHOH, and $SO_2NHR$ where R is methyl, ethyl, $CF_3$, $CHF_2$, or $CHF_3$; where HetAr is benzamidazolyl, benzoxazolyl, imidazopyridinyl, or imidazopyramidinyl; and where $n_1$ is 0-2, $n_2$ is 0-5, and $n_3$ is 0-3.

Compounds according to aspects of the present disclosure include, or consist of, structural formula (I):

where X is O, NH, or S; where $R_1$, $R_2$, and $R_3$, are each independently selected from the group consisting of H, Br, F, methyl, Cl, OH, CN, $NH_2$, and $CF_3$; where $R_4$ is H, methyl, isopropyl, phenyl, ethyl, cyclopropyl, cyclohexyl, or methylcyclohexyl; where $R_5$ is COOH, $CO_2R$, $SO_3H$, $SO_2NH_2$, $PO_3H$, $CONH_2$, CONHOH, and $SO_2NHR$ where R is methyl, ethyl, $CF_3$, $CHF_2$, or $CHF_3$; where HetAr is benzamidazolyl, benzoxazolyl, imidazopyridinyl, or imidazopyramidinyl; and where $n_1$ is 0-2, $n_2$ is 0-5, and $n_3$ is 0-3.

Isomers, salts, and derivatives of compounds including, or consisting of, structural formula (I) are disclosed herein.

Compounds according to aspects of the present disclosure include, or consist of, structural formula (II):

Isomers, salts, and derivatives of compounds including, or consisting of, structural formula (II) are disclosed herein.

According to aspects of the present disclosure, a salt of a compound including, or consisting of, structural formula (I) or (II) is a pharmaceutically acceptable salt.

According to aspects of the present disclosure, a derivative of a compound including, or consisting of, structural formula (I) or (II) is an ester, amide, or hydrate of the compound.

Compounds according to aspects of the present disclosure encompass stereoisomers of a compound including, or consisting of, structural formula (I) and/or (II). Compositions and pharmaceutical compositions according to the present disclosure encompass the individual enantiomers of a compound including, or consisting of, structural formula (I) and/or (II), as well as wholly or partially racemic mixtures of any of these.

Pharmaceutical compositions according to aspects of the present disclosure include a compound including, or consisting of, structural formula (I) or (II), a salt, derivative, or isomer thereof; and a pharmaceutically acceptable carrier.

According to aspects of the present disclosure, a compound including, or consisting of, structural formula (I) or (II), a salt, derivative, or isomer thereof; or a pharmaceutical composition including a compound including, or consisting of, structural formula (I) or (II), a salt, derivative, or isomer thereof; is an inhibitor of CXCR4 and one or more of: TNF, IL-1beta, IL-6, and IL-8.

Methods of treatment of a subject having, or suspected of having, cancer, according to aspects of the present disclosure include administering an effective amount of a pharmaceutical composition which includes, or consists of, a compound having structural formula (I) or (II), a salt, isomer, or derivative thereof, to the subject.

According to aspects of the present disclosure, administering the effective amount of the pharmaceutical composition includes systemic and/or local administration.

According to aspects of the present disclosure, methods of treatment of a subject having, or suspected of having, cancer further include assaying one or more of: CXCR4, TNF, IL-1beta, IL-6, and IL-8 in a subject sample.

According to aspects of the present disclosure, methods of treatment of a subject having, or suspected of having, cancer further include assaying one or more of: CXCR4, TNF, IL-1beta, IL-6, and IL-8 in a subject sample prior to, after, or both prior to and after, administering the effective amount of the pharmaceutical composition.

Methods of treatment of a subject having, or suspected of having, cancer, according to aspects of the present disclosure include administering an effective amount of 1) a pharmaceutical composition which includes a compound including, or consisting of, structural formula (I) or (II), a salt, isomer, or derivative thereof; and 2) additional therapeutic agent, to the subject.

According to aspects of the present disclosure, the additional therapeutic agent includes an additional inhibitor of a proinflammatory cytokine or chemokine.

According to aspects of the present disclosure, the additional inhibitor includes a nucleic acid inhibitor, an antibody, an antigen-binding antibody fragment, an aptamer, an inorganic or organic small molecule inhibitor, or a combination of any two or more thereof.

According to aspects of the present disclosure, the additional therapeutic agent includes an anti-cancer agent.

Methods of treatment of a subject having, or suspected of having, cancer, according to aspects of the present disclosure include administering an effective amount of 1) a pharmaceutical composition which includes a compound including, or consisting of, structural formula (I) or (II), a salt, isomer, or derivative thereof; and 2) additional therapeutic agent, to the subject; and further includes administering an adjunct anti-cancer treatment to the subject.

According to aspects of the present disclosure, the adjunct anti-cancer therapy includes surgery and/or radiation treatment.

According to aspects of the present disclosure, the cancer is prostate cancer.

According to aspects of the present disclosure, the cancer is castration resistant prostate cancer.

DETAILED DESCRIPTION OF THE INVENTION

Scientific and technical terms used herein are intended to have the meanings commonly understood by those of ordinary skill in the art. Such terms are found defined and used in context in various standard references illustratively including J. Sambrook and D. W. Russell, Molecular Cloning: A Laboratory Manual, Cold Spring Harbor Laboratory Press; 3rd Ed., 2001; F. M. Ausubel, Ed., Short Protocols in Molecular Biology, Current Protocols, 5th Ed., 2002; B. Alberts et al., Molecular Biology of the Cell, 4th Ed., Garland, 2002; D. L. Nelson and M. M. Cox, Lehninger Principles of Biochemistry, 4th Ed., W. H. Freeman & Company, 2004; J.-H. Fuhrhop et al. (Eds.), Organic Synthesis, Concepts and Methods, 3$^{rd}$ Ed., Wiley-VCH Cerlag GmbH & Co. KGaA, 2003; Herdewijn, P. (Ed.), Oligonucleotide Synthesis: Methods and Applications, Methods in Molecular Biology, Humana Press, 2004; D. J. Taxman (ed.), siRNA Design, Methods and Protocols, Humana Press, 2012; Harlow, E. and Lane, D., Antibodies: A Laboratory Manual, Cold Spring Harbor Laboratory Press, 1988; J. D. Pound (Ed.) Immunochemical Protocols, Methods in Molecular Biology, Humana Press, 2nd ed., 1998; B. K. C. Lo (Ed.); A Adejare (Ed.), Remington: The Science and Practice of Pharmacy, Elsevier, 23rd Ed., 2021; L. V. Allen, Jr. et al., Ansel's Pharmaceutical Dosage Forms and Drug Delivery Systems, 11th Ed., Wolters Kluwer, 2016; and L. Brunton et al., Goodman & Gilman's The Pharmacological Basis of Therapeutics, McGraw-Hill Education, 13th Ed., 2018.

The singular terms "a," "an," and "the" are not intended to be limiting and include plural referents unless explicitly stated otherwise or the context clearly indicates otherwise.

The term "pro-inflammatory factor" as used herein refers to one or more of a pro-inflammatory cytokine, a pro-inflammatory chemokine, a pro-inflammatory cytokine receptor, a pro-inflammatory chemokine receptor, or a stimulator of any of these.

The terms "includes," "comprises," "including," "comprising," "has," "having," and grammatical variations thereof, when used in this specification, are not intended to be limiting, and specify the presence of stated features, elements, and/or components, but do not preclude the presence or addition of one or more other features, elements, components, and/or groups thereof.

Particular combinations of features are recited in the claims and/or disclosed in the specification, and these combinations of features are not intended to limit the disclosure of various aspects. Combinations of such features not specifically recited in the claims and/or disclosed in the specification. Although each dependent claim listed below may directly depend on only one claim, the disclosure of various aspects includes each dependent claim in combination with every other claim in the claim set. As used herein, a phrase referring to "at least one of" a list of items refers to any combination of those items, including single members. As an example, "at least one of: a, b, or c" is intended to cover a alone; b alone; c alone, a and b, a, b, and c, b and c, a and c, as well as any combination with multiples of the same element, such as a and a; a, a, and a; a, a, and b; a, a, and c; a, b, and b; a, c, and c; and any other combination or ordering of a, b, and c).

The term "about" as used herein in reference to a number is used herein to include numbers which are greater, or less than, a stated or implied value by 1%, 5%, 10%, or 20%.

Compounds are provided according to aspects of the present disclosure having structural formula (I):

where X is O, NH, or S; where $R_1$, $R_2$, and $R_3$, are each independently selected from the group consisting of H, Br, F, methyl, Cl, OH, CN, $NH_2$, and $CF_3$; where $R_4$ is H, $C_1$-$C_6$ unsubstituted or substituted, alkyl, cycloalkyl, aryl, phenyl, heteroalkyl, heterocycloalkyl, or heteroaryl; where $R_5$ is COOH, $CO_2R$, $SO_3H$, $SO_2NH_2$, $PO_3H$, $CONH_2$, CONHOH, and $SO_2NHR$ where R is methyl, ethyl, $CF_3$, $CHF_2$, or CHF$_3$; where HetAr is benzamidazolyl, benzoxazolyl, imidazopyridinyl, or imidazopyramidinyl; and where n$_1$ is 0-2, n$_2$ is 0-5, and n$_3$ is 0-3.

Compounds according to aspects of the present disclosure having structural formula (I) are inhibitors of C—X—C motif chemokine receptor 4 (CXCR4) and one or more of: tumor necrosis factor-alpha (TNF-alpha), interleukin-1beta (IL-1beta), interleukin-6 (IL-6), and interleukin-8 (IL-8).

The term "inhibitor of CXCR4 and one or more of: TNF-alpha, IL-1beta, IL-6, and IL-8" refers to activity of a compound to specifically inhibit particular molecules, i.e. of CXCR4 and one or more of: TNF-alpha, IL-1beta, IL-6, and IL-8. An inhibitor of CXCR4 and one or more of: TNF-alpha, IL-1beta, IL-6, and IL-8 reduces a level and/or activity of its target, i.e. of CXCR4 and one or more of: TNF-alpha, IL-1beta, IL-6, and IL-8, by at least 10%, 20%, 30%, 40%, 50%, 60%, 70%, 80%, 90%, 95%, 99% or more, compared to a control, such as absence of the inhibitor.

Compounds are provided according to aspects of the present disclosure having structural formula (I):

where X is O, NH, or S; where R$_1$, R$_2$, and R$_3$, are each independently selected from the group consisting of H, Br, F, methyl, Cl, OH, CN, NH$_2$, and CF$_3$; where R$_4$ is H, methyl, isopropyl, phenyl, ethyl, cyclopropyl, cyclohexyl, or methylcyclohexyl; where R$_5$ is COOH, CO$_2$R, SO$_3$H, SO$_2$NH$_2$, PO$_3$H, CONH$_2$, CONHOH, and SO$_2$NHR where R is methyl, ethyl, CF$_3$, CHF$_2$, or CHF$_3$; where HetAr is benzamidazolyl, benzoxazolyl, imidazopyridinyl, or imidazopyramidinyl; and where n$_1$ is 0-2, n$_2$ is 0-5, and n$_3$ is 0-3.

Compounds are provided according to aspects of the present disclosure having structural formula (II):

According to aspects of the present disclosure, isomers, salts, and derivatives of compounds of structural formulas (I) and (II) are provided.

According to aspects of the present disclosure, pharmaceutically acceptable salts of compounds of structural formulas (I) and (II) are provided.

The term "pharmaceutically acceptable salt" refers to salts which are suitable for use in a subject without undue toxicity or irritation to the subject and which are effective for their intended use.

Pharmaceutically acceptable salts include pharmaceutically acceptable acid addition salts and base addition salts. Pharmaceutically acceptable salts are well-known in the art, such as those detailed in S. M. Berge et al., J. Pharm. Sci., 66:1-19, 1977. Exemplary pharmaceutically acceptable salts are those suitable for use in a subject without undue toxicity or irritation to the subject and which are effective for their intended use which are formed with inorganic acids such as hydrochloric acid, hydrobromic acid, hydroiodic acid, nitric acid, phosphoric acid, sulfuric acid and sulfamic acid; organic acids such as acetic acid, adipic acid, alginic acid, ascorbic acid, aspartic acid, benzenesulfonic acid, benzoic acid, 2-acetoxybenzoic acid, butyric acid, camphoric acid, camphorsulfonic acid, cinnamic acid, citric acid, digluconic acid, ethanesulfonic acid, formic acid, fumaric acid, glutamic acid, glycolic acid, glycerophosphoric acid, hemisulfic acid, heptanoic acid, hexanoic acid, 2-hydroxyethanesulfonic acid (isethionic acid), lactic acid, maleic acid, hydroxymaleic acid, malic acid, malonic acid, mandelic acid, mesitylenesulfonic acid, methanesulfonic acid, naphthalenesulfonic acid, nicotinic acid, 2-naphthalenesulfonic acid, oxalic acid, pamoic acid, pectinic acid, phenylacetic acid, 3-phenylpropionic acid, picric acid, pivalic acid, propionic acid, pyruvic acid, pyruvic acid, salicylic acid, stearic acid, succinic acid, sulfanilic acid, tartaric acid, p-toluenesulfonic acid, trichloroacetic acid, trifluoroacetic acid and undecanoic acid; inorganic bases such as ammonia, hydroxide, carbonate, and bicarbonate of ammonium; organic bases such as primary, secondary, tertiary and quaternary amine compounds ammonium, arginine, betaine, choline, caffeine, diolamine, diethylamine, diethanolamine, 2-dimethylaminoethanol, 2-diethylaminoethanol, dicyclohexylamine, dicyclohexylamine, dibenzylamine, N, N-dibenzylphenethylamine, 1-ephenamine, N, N'-dibenzylethylenediamine, ethanolamine, ethylamine, ethylenediamine, glucosamine, histidine, hydrabamine, isopropylamine, 1H-imidazole, lysine, methylamine, N-ethylpiperidine, N-methylpiperidine, N-methylmorpholine, N, N-dimethylaniline, piperazine, trolamine, methylglucamine, purines, piperidine, pyridine, theobromine, tetramethylammonium compounds, tetraethyl ammonium compounds, trimethylamine, triethylamine, tripropylamine and tributylamine and metal cations such as aluminum, calcium, copper, iron, lithium, magnesium, manganese, potassium, sodium, and zinc.

According to aspects, a derivative of a compound of the present disclosure is an ester, amide, or hydrate of a compound including, or consisting of, structural formula (I), (II), or a salt, or isomer, thereof.

Synthesis

Figure 1:
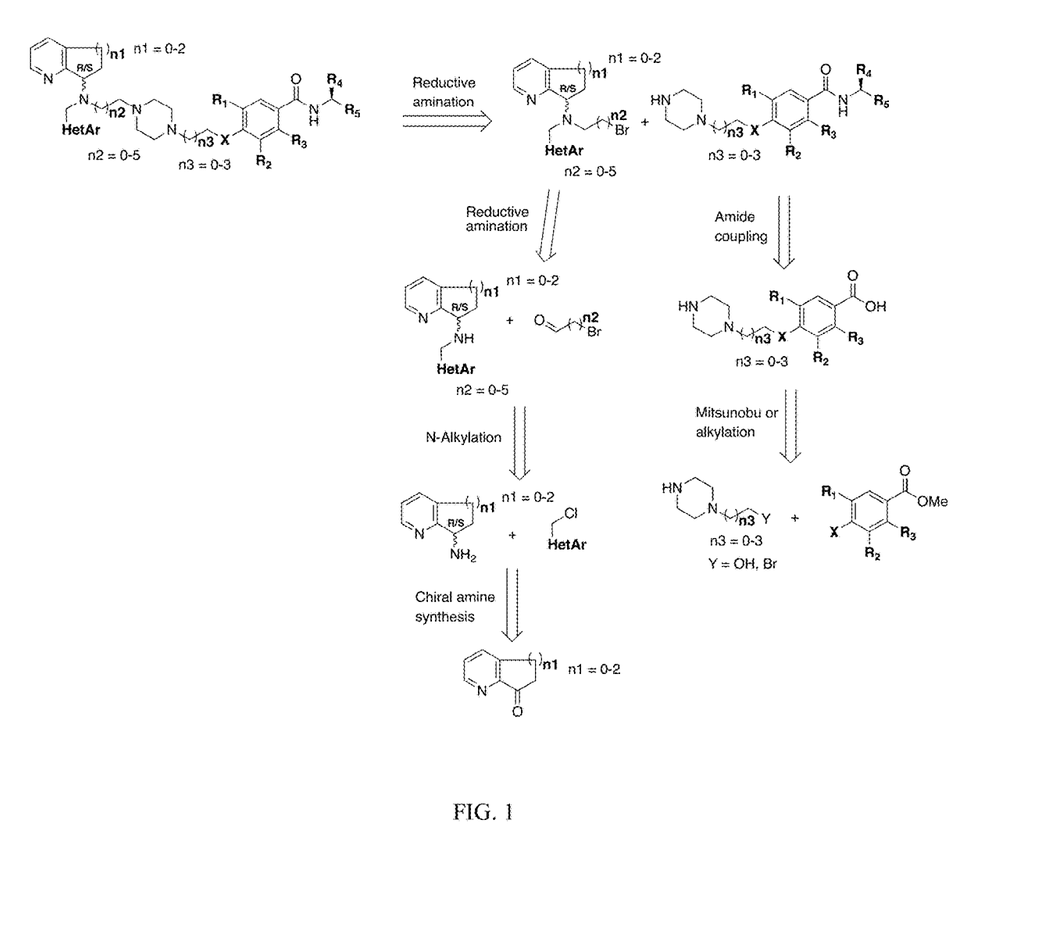
FIG. 1 is a diagram showing a retrosynthetic scheme for compounds of structural formula (I)

A retrosynthetic scheme for compounds comprising or consisting of structural formula (I), a salt, isomer, or derivative thereof, is shown in FIG. 1.

Figure 2:
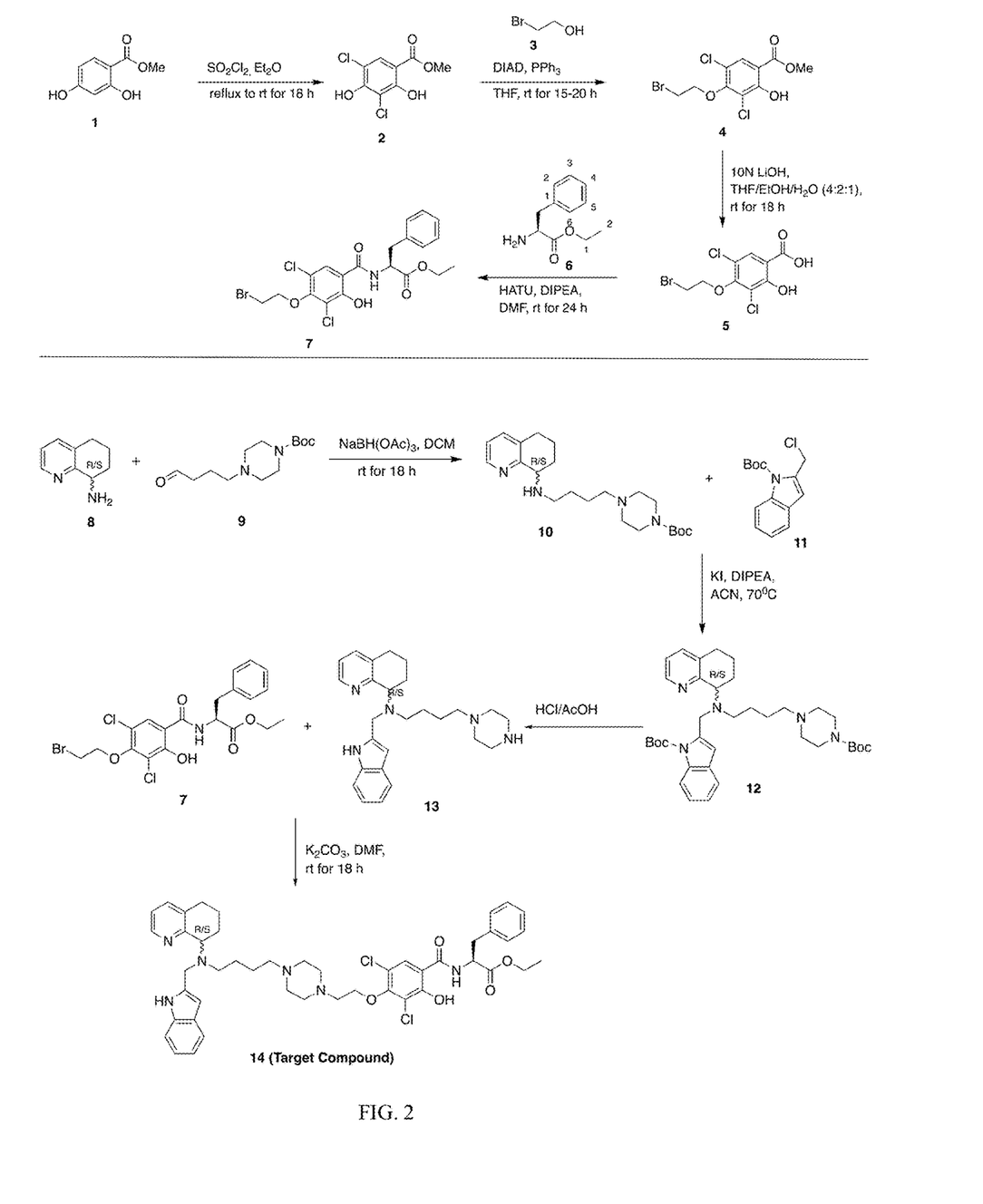
FIG. 2 is a diagram showing an exemplary synthetic scheme for a compound having structural formula (II).

FIG. 2 is a diagram showing an exemplary synthetic scheme for a compound comprising or consisting of structural formula (II) or a salt, isomer, or derivative thereof.

Pharmaceutical Compositions

Pharmaceutical compositions are provided which include, or consist of, a compound of the present disclosure, a salt, derivative, or isomer thereof; and a pharmaceutically acceptable carrier.

A pharmaceutical composition according to aspects includes about 0.1-99% of a compound of the present disclosure, and/or a salt, derivative, or isomer thereof. According to aspects of the present disclosure, a pharmaceutically acceptable carrier is included in a pharmaceutical composition with the compound, and/or a salt, derivative, or isomer thereof.

A pharmaceutical composition of the present disclosure may be in any dosage form suitable for administration to a subject, illustratively including solid, semi-solid and liquid dosage forms such as tablets, capsules, powders, granules, suppositories, pills, solutions, suspensions, ointments, lotions, creams, gels, pastes, sprays and aerosols.

Liposomes and emulsions are well-known types of pharmaceutical formulations that can be used to deliver a pharmaceutical agent, particularly a hydrophobic pharmaceutical agent.

Pharmaceutical compositions of the present disclosure generally include a pharmaceutically acceptable carrier such as an excipient, diluent and/or vehicle.

Delayed release formulations of compositions and delayed release systems, such as semipermeable matrices of solid hydrophobic polymers can be used.

The term "pharmaceutically acceptable carrier" may refer to a carrier which is suitable for use in a subject without undue toxicity or irritation to the subject and which is compatible with other ingredients included in a pharmaceutical composition. Pharmaceutically acceptable carriers, methods for making pharmaceutical compositions and various dosage forms, as well as modes of administration are well-known in the art, for example as detailed in Pharmaceutical Dosage Forms: Tablets, eds. H. A. Lieberman et al., New York: Marcel Dekker, Inc., 1989; and in L. V. Allen, Jr. et al., Ansel's Pharmaceutical Dosage Forms and Drug Delivery Systems, 11th Ed., Wolters Kluwer, 2016; A Adejare (Ed.), Remington: The Science and Practice of Pharmacy, Elsevier, 23rd Ed., 2021; and L. Brunton et al., Goodman & Gilman's The Pharmacological Basis of Therapeutics, McGraw-Hill Education, 13th ed., 2018.

A solid dosage form for administration or for suspension in a liquid prior to administration illustratively includes capsules, tablets, powders, and granules. In such solid dosage forms, one or more active agents, is admixed with at least one carrier illustratively including a buffer such as, for example, sodium citrate or an alkali metal phosphate illustratively including sodium phosphates, potassium phosphates and calcium phosphates; a filler such as, for example, starch, lactose, sucrose, glucose, mannitol, and silicic acid; a binder such as, for example, carboxymethylcellulose, alginates, gelatin, polyvinylpyrrolidone, sucrose, and acacia; a humectant such as, for example, glycerol; a disintegrating agent such as, for example, agar-agar, calcium carbonate, plant starches such as potato or tapioca starch, alginic acid, certain complex silicates, and sodium carbonate; a solution retarder such as, for example, paraffin; an absorption accelerator such as, for example, a quaternary ammonium compound; a wetting agent such as, for example, cetyl alcohol, glycerol monostearate, and a glycol; an adsorbent such as, for example, kaolin and bentonite; a lubricant such as, for example, talc, calcium stearate, magnesium stearate, a solid polyethylene glycol or sodium lauryl sulfate; a preservative such as an antibacterial agent and an antifungal agent, including for example, sorbic acid, gentamycin and phenol; and a stabilizer such as, for example, sucrose, EDTA, EGTA, and an antioxidant.

Solid dosage forms may optionally include a coating such as an enteric coating. The enteric coating is typically a polymeric material. Preferred enteric coating materials have the characteristics of being bioerodible, gradually hydrolyzable and/or gradually water-soluble polymers. The amount of coating material applied to a solid dosage generally dictates the time interval between ingestion and drug release. A coating is applied having a thickness such that the entire coating does not dissolve in the gastrointestinal fluids at pH below 3 associated with stomach acids, yet dissolves above pH 3 in the small intestine environment. It is expected that any anionic polymer exhibiting a pH-dependent solubility profile is readily used as an enteric coating in the practice of the present disclosure to achieve delivery of the active agent to the lower gastrointestinal tract. The selection of the specific enteric coating material depends on properties such as resistance to disintegration in the stomach; impermeability to gastric fluids and active agent diffusion while in the stomach; ability to dissipate at the target intestine site; physical and chemical stability during storage; non-toxicity; and ease of application.

Suitable enteric coating materials illustratively include cellulosic polymers such as hydroxypropyl cellulose, hydroxyethyl cellulose, hydroxypropyl methyl cellulose, methyl cellulose, ethyl cellulose, cellulose acetate, cellulose acetate phthalate, cellulose acetate trimellitate, hydroxypropylmethyl cellulose phthalate, hydroxypropylmethyl cellulose succinate and carboxymethylcellulose sodium; acrylic acid polymers and copolymers, preferably formed from acrylic acid, methacrylic acid, methyl acrylate, ammonium methylacrylate, ethyl acrylate, methyl methacrylate and/or ethyl; vinyl polymers and copolymers such as polyvinyl pyrrolidone, polyvinyl acetate, polyvinylacetate phthalate, vinylacetate crotonic acid copolymer, and ethylene-vinyl acetate copolymers; shellac; and combinations thereof. A particular enteric coating material includes acrylic acid polymers and copolymers described for example U.S. Pat. No. 6,136,345.

The enteric coating optionally contains a plasticizer to prevent the formation of pores and cracks that allow the penetration of the gastric fluids into the solid dosage form. Suitable plasticizers illustratively include triethyl citrate (Citroflex 2), triacetin (glyceryl triacetate), acetyl triethyl citrate (Citroflec A2), Carbowax 400 (polyethylene glycol 400), diethyl phthalate, tributyl citrate, acetylated monoglycerides, glycerol, fatty acid esters, propylene glycol, and dibutyl phthalate. In particular, a coating composed of an anionic carboxylic acrylic polymer typically contains approximately 10% to 25% by weight of a plasticizer, particularly dibutyl phthalate, polyethylene glycol, triethyl citrate and triacetin. The coating can also contain other coating excipients such as detackifiers, antifoaming agents, lubricants (e.g., magnesium stearate), and stabilizers (e.g. hydroxypropylcellulose, acids or bases) to solubilize or disperse the coating material, and to improve coating performance and the coated product.

Liquid dosage forms for oral administration include one or more active agents and a pharmaceutically acceptable carrier formulated as an emulsion, solution, suspension, syrup, or elixir. A liquid dosage form of a composition of the present disclosure may include a colorant, a stabilizer, a wetting agent, an emulsifying agent, a suspending agent, a sweetener, a flavoring, or a perfuming agent.

For example, a composition for parenteral administration may be formulated as an injectable liquid. Examples of suitable aqueous and nonaqueous carriers include water, ethanol, polyols such as propylene glycol, polyethylene glycol, glycerol, and the like, suitable mixtures thereof; vegetable oils such as olive oil; and injectable organic esters such as ethyloleate. Proper fluidity can be maintained, for example, by the use of a coating such as lecithin, by the maintenance of a desirable particle size in the case of dispersions, and/or by the use of a surfactant, such as sodium lauryl sulfate. A stabilizer is optionally included such as, for example, sucrose, EDTA, EGTA, and an antioxidant.

For topical administration, a composition can be formulated for administration to the skin such as for local effect, and/or as a "patch" formulation for transdermal delivery. Pharmaceutical formulations suitable for topical administration include, for example, ointments, lotions, creams, gels, pastes, sprays and powders. Ointments, lotions, creams, gels and pastes can include, in addition to one or more active agents, a base such as an absorption base, water-removable base, water-soluble base or oleaginous base and excipients such as a thickening agent, a gelling agent, a colorant, a stabilizer, an emulsifying agent, a suspending agent, a sweetener, a flavoring, or a perfuming agent.

Transdermal formulations can include percutaneous absorption enhancers such as acetone, azone, dimethyl acetamide, dimethyl formamide, dimethyl sulfoxide, ethanol, oleic acid, polyethylene glycol, propylene glycol and sodium lauryl sulfate. Ionotophoresis and/or sonophoresis can be used to enhance transdermal delivery.

Powders and sprays for topical administration of one or more active agents can include excipients such as talc, lactose and one or more silicic acids. Sprays can include a pharmaceutical propellant such as a fluorinated hydrocarbon propellant, carbon dioxide, or a suitable gas. Alternatively, a spray can be delivered from a pump-style spray device which does not require a propellant. A spray device delivers a metered dose of a composition contained therein, for example, using a valve for regulation of a delivered amount.

Ophthalmic formulations of one or more active agents can include ingredients such as a preservative, a buffer and a thickening agent.

Suitable surface-active agents useful as a pharmaceutically acceptable carrier or excipient in the pharmaceutical compositions of the present disclosure include non-ionic, cationic and/or anionic surfactants having good emulsifying, dispersing and/or wetting properties. Suitable anionic surfactants include both water-soluble soaps and water-soluble synthetic surface-active agents. Suitable soaps are alkaline or alkaline-earth metal salts, non-substituted or substituted ammonium salts of higher fatty acids (C10-C22), e.g. the sodium or potassium salts of oleic or stearic acid, or of natural fatty acid mixtures obtainable form coconut oil or tallow oil. Synthetic surfactants include sodium or calcium salts of polyacrylic acids; fatty sulphonates and sulphates; sulphonated benzimidazole derivatives and alkylarylsulphonates. Fatty sulphonates or sulphates are usually in the form of alkaline or alkaline-earth metal salts, non-substituted ammonium salts or ammonium salts substituted with an alkyl or acyl radical having from 8 to 22 carbon atoms, e.g. the sodium or calcium salt of lignosulphonic acid or dodecylsulphonic acid or a mixture of fatty alcohol sulphates obtained from natural fatty acids, alkaline or alkaline-earth metal salts of sulphuric or sulphonic acid esters (such as sodium lauryl sulphate) and sulphonic acids of fatty alcohol/ethylene oxide adducts. Suitable sulphonated benzimidazole derivatives preferably contain 8 to 22 carbon atoms. Examples of alkylarylsulphonates are the sodium, calcium or alcanolamine salts of dodecylbenzene sulphonic acid or dibutyl-naphthalene sulphonic acid or a naphthalene-sulphonic acid/formaldehyde condensation product. Also suitable are the corresponding phosphates, e.g. salts of phosphoric acid ester and an adduct of p-nonylphenol with ethylene and/or propylene oxide, or phospholipids. Suitable phospholipids for this purpose are the natural (originating from animal or plant cells) or synthetic phospholipids of the cephalin or lecithin type such as e.g. phosphatidyletha-nolamine, phosphatidylserine, phosphatidylglycerine, lysolecithin, cardiolipin, dioctanylphosphatidylcholine, dipalmitoylphosphatidyl-choline and their mixtures.

Suitable non-ionic surfactants useful as pharmaceutically acceptable carriers or excipients in the pharmaceutical compositions of the present disclosure include polyethoxylated and polypropoxylated derivatives of alkylphenols, fatty alcohols, fatty acids, aliphatic amines or amides containing at least 12 carbon atoms in the molecule, alkylarenesulphonates and dialkylsulphosuccinates, such as polyglycol ether derivatives of aliphatic and cycloaliphatic alcohols, saturated and unsaturated fatty acids and alkylphenols, said derivatives preferably containing 3 to 10 glycol ether groups and 8 to 20 carbon atoms in the (aliphatic) hydrocarbon moiety and 6 to 18 carbon atoms in the alkyl moiety of the alkylphenol. Further suitable non-ionic surfactants are water-soluble adducts of polyethylene oxide with poylypropylene glycol, ethylenediaminopolypropylene glycol containing 1 to 10 carbon atoms in the alkyl chain, which adducts contain 20 to 250 ethyleneglycol ether groups and/or 10 to 100 propyleneglycol ether groups. Such compounds usually contain from 1 to 5 ethyleneglycol units per propyleneglycol unit. Representative examples of non-ionic surfactants are nonylphenol-polyethoxyethanol, castor oil polyglycolic ethers, polypropylene/polyethylene oxide adducts, tributylphenoxypolyethoxyethanol, polyethyleneglycol and octylphenoxypolyethoxyethanol. Fatty acid esters of polyethylene sorbitan (such as polyoxyethylene sorbitan trioleate), glycerol, sorbitan, sucrose and pentaerythritol are also suitable non-ionic surfactants.

Suitable cationic surfactants useful as pharmaceutically acceptable carriers or excipients in the pharmaceutical compositions of the present disclosure include quaternary ammonium salts, preferably halides, having 4 hydrocarbon radicals optionally substituted with halo, phenyl, substituted phenyl or hydroxy; for instance quaternary ammonium salts containing as N-substituent at least one $C_8$-$C_{22}$ alkyl radical (e.g. cetyl, lauryl, palmityl, myristyl, oleyl and the like) and, as further substituents, unsubstituted or halogenated lower alkyl, benzyl and/or hydroxy-lower alkyl radicals.

A more detailed description of surface-active agents suitable for this purpose may be found for instance in "McCutcheon's Detergents and Emulsifiers Annual" (MC Publishing Crop., Ridgewood, New Jersey, 1981), "Tensid-Taschenbuch", 2nd ed. (Hanser Verlag, Vienna, 1981) and "Encyclopedia of Surfactants (Chemical Publishing Co., New York, 1981).

Structure-forming, thickening or gel-forming agents may be included into the pharmaceutical compositions and combined preparations of the disclosure. Suitable such agents are in particular highly dispersed silicic acid, such as the product commercially available under the trade name Aerosil; bentonites; tetraalkyl ammonium salts of montmorillonites (e.g., products commercially available under the trade name Bentone), wherein each of the alkyl groups may contain from 1 to 20 carbon atoms; cetostearyl alcohol and modified castor oil products (e.g. the product commercially available under the trade name Antisettle).

In particular aspects, a pharmaceutically acceptable carrier is a particulate carrier such as lipid particles including liposomes, micelles, unilamellar or mulitlamellar vesicles; polymer particles such as hydrogel particles, polyglycolic acid particles or polylactic acid particles; inorganic particles such as calcium phosphate particles such as described in for example U.S. Pat. No. 5,648,097; and inorganic/organic particulate carriers such as described for example in U.S. Pat. No. 6,630,486.

A particulate pharmaceutically acceptable carrier can be selected from among a lipid particle; a polymer particle; an inorganic particle; and an inorganic/organic particle. A mixture of particle types can also be included as a particulate pharmaceutically acceptable carrier.

A particulate carrier is typically formulated such that particles have an average particle size in the range of about 1 nm-10 microns. In particular aspects, a particulate carrier is formulated such that particles have an average particle size in the range of about 1 nm-100 nm.

Detailed information concerning customary ingredients, equipment and processes for preparing dosage forms is found in Pharmaceutical Dosage Forms: Tablets, eds. H. A. Lieberman et al., New York: Marcel Dekker, Inc., 1989; and in L. V. Allen, Jr. et al., Ansel's Pharmaceutical Dosage Forms and Drug Delivery Systems, 11th Ed., Wolters Kluwer, 2016; A Adejare (Ed.), Remington: The Science and Practice of Pharmacy, Elsevier, 23rd Ed., 2021; and L. Brunton et al., Goodman & Gilman's The Pharmacological Basis of Therapeutics, McGraw-Hill Education, 13th Ed., 2018.

Additional Therapeutic Agents

Pharmaceutical compositions are provided which include a compound of the present disclosure, and/or a salt, derivative, and/or isomer thereof, one or more additional therapeutic agents, and a pharmaceutically acceptable carrier.

The term "additional therapeutic agent" is used herein to refer to a chemical compound, a mixture of chemical compounds, a biological macromolecule (such as a nucleic acid, an antibody, a protein or portion thereof, e.g., a peptide), or an extract made from biological materials such as bacteria, plants, fungi, or animal (particularly mammalian) cells or tissues which is a biologically, physiologically, or pharmacologically active substance (or substances) that acts locally or systemically in a subject.

Additional therapeutic agents include, but are not limited to, antibiotics, antivirals, antineoplastic agents, analgesics, antipyretics, antidepressants, antipsychotics, anti-cancer agents, antihistamines, anti-osteoporosis agents, anti-osteonecrosis agents, antiinflammatory agents, anxiolytics, chemotherapeutic agents, diuretics, growth factors, hormones, non-steroidal anti-inflammatory agents, steroids and vasoactive agents.

An additional pharmaceutical agent is an anti-cancer agent according to aspects of the present disclosure.

Anti-cancer agents are described, for example, in L. Brunton et al., Goodman & Gilman's The Pharmacological Basis of Therapeutics, McGraw-Hill Education, 13th Ed., 2018.

Anti-cancer agents illustratively include acivicin, aclarubicin, acodazole, acronine, adozelesin, aldesleukin, alitretinoin, allopurinol, altretamine, ambomycin, ametantrone, amifostine, aminoglutethimide, amsacrine, anastrozole, anthramycin, arsenic trioxide, asparaginase, asperlin, azacitidine, azetepa, azotomycin, batimastat, benzodepa, bevacizumab, bicalutamide, bisantrene, bisnafide dimesylate, bizelesin, bleomycin, brequinar, bropirimine, busulfan, cactinomycin, calusterone, capecitabine, caracemide, carbetimer, carboplatin, carmustine, carubicin, carzelesin, cedefingol, celecoxib, chlorambucil, cirolemycin, cisplatin, cladribine, cobimetinib, crisnatol mesylate, cyclophosphamide, cytarabine, dacarbazine, dactinomycin, daunorubicin, decitabine, dexormaplatin, dezaguanine, dezaguanine mesylate, diaziquone, docetaxel, doxorubicin, droloxifene, dromostanolone, duazomycin, edatrexate, eflomithine, elsamitrucin, enloplatin, enpromate, epipropidine, epirubicin, erbulozole, esorubicin, estramustine, etanidazole, etoposide, etoprine, fadrozole, fazarabine, fenretinide, floxuridine, fludarabine, fluorouracil, flurocitabine, fosquidone, fostriecin, fulvestrant, gemcitabine, hydroxyurea, idarubicin, ifosfamide, ilmofosine, interleukin II (IL-2, including recombinant interleukin II or rIL2), interferon alfa-2a, interferon alfa-2b, interferon alfa-n1, interferon alfa-n3, interferon beta-Ia, interferon gamma-Ib, iproplatin, irinotecan, lanreotide, letrozole, leuprolide, liarozole, lometrexol, lomustine, losoxantrone, masoprocol, maytansine, mechlorethamine hydrochlride, megestrol, melengestrol acetate, melphalan, menogaril, mercaptopurine, methotrexate, metoprine, meturedepa, mitindomide, mitocarcin, mitocromin, mitogillin, mitomalcin, mitomycin, mitosper, mitotane, mitoxantrone, mycophenolic acid, nelarabine, nocodazole, nogalamycin, ormnaplatin, oxisuran, paclitaxel, pegaspargase, peliomycin, pentamustine, peplomycin, perfosfamide, pipobroman, piposulfan, piroxantrone hydrochloride, plicamycin, plomestane, porfimer, porfiromycin, prednimustine, procarbazine, puromycin, pyrazofurin, riboprine, rogletimide, safingol, semustine, simtrazene, sparfosate, sparsomycin, spirogermanium, spiromustine, spiroplatin, streptonigrin, streptozocin, sulofenur, talisomycin, tamoxifen, tecogalan, tegafur, teloxantrone, temoporfin, teniposide, teroxirone, testolactone, thiamiprine, thioguanine, thiotepa, tiazofurin, tirapazamine, topotecan, toremifene, trestolone, triciribine, trimetrexate, triptorelin, tubulozole, uracil mustard, uredepa, vapreotide, vemurafenib, verteporfin, vinblastine, vincristine sulfate, vindesine, vinepidine, vinglycinate, vinleurosine, vinorelbine, vinrosidine, vinzolidine, vorozole, zeniplatin, zinostatin, zoledronate, and zorubicin.

An anti-cancer agent administered according to aspects of the present disclosure can be an immune checkpoint inhibitor.

Immune checkpoint inhibitors include, but are not limited to, PD-1 inhibitors, PD-L1 inhibitors, and CTLA4 inhibitors.

The term "immune checkpoint inhibitor" refers to a substance having activity to specifically inhibit immune checkpoint activity, including inhibition of T cells expressing PD-1 to suppress immune reaction to cancer cells. An immune checkpoint inhibitor can be a PD-1 inhibitor, a PD-1 ligand (PD-L1) inhibitor, or a CTLA4 inhibitor.

PD-L1 inhibitors are anti-PD-L1 antibodies such as, but not limited to, atezolizumab, avelumab, and durvalumab; and an antigen-binding fragment of any one of the foregoing. siRNA or a CRISPR/Cas knockdown construct directed to PD-L1 can be used to inhibit PD-L1.

CTLA4 inhibitors are anti-CTLA4 antibodies such as, but not limited to ipilimumab and an antigen-binding fragment thereof. siRNA or a CRISPR/Cas knockdown construct directed to CTLA4 can be used to inhibit CTLA4.

PD-1 inhibitors are anti-PD-1 antibodies such as, but not limited to, nivolumab, and pembrolizumab; and an antigen-binding fragment of any one of the foregoing. siRNA or a CRISPR/Cas knockdown construct directed to PDL1 can be used to inhibit PD-1.

An additional pharmaceutical agent can be an additional inhibitor of one or more pro-inflammatory factors, particularly pro-inflammatory chemokines, pro-inflammatory cytokines, pro-inflammatory cytokine receptors, or pro-inflammatory chemokine receptors, according to aspects of the present disclosure.

An additional inhibitor of one or more pro-inflammatory factors can be any molecule, chemical entity, biological entity, composition, or agent, having activity to specifically inhibit a specified pro-inflammatory factor, particularly one or more pro-inflammatory chemokines, pro-inflammatory cytokines, pro-inflammatory cytokine receptors, or pro-inflammatory chemokine receptors.

An additional inhibitor of one or more pro-inflammatory factors can be, without limitation, an additional inhibitor of one or more of: IL-1β, IL-6, IL-8, interleukin-10 (IL-10), stromal cell-derived factor-1α (SDF-1α, also known as C—X—C motif chemokine ligand 12), matrix metallopeptidase 9 (MMP-9), ENA-78 (also known as C—X—C motif chemokine ligand 5), receptor for advanced glycation end products (RAGE), TNF-α, human epidermal growth factor receptor 2, HER2, also known as receptor tyrosine-protein kinase erbB2 or CD340), CXCR4, and leptin.

An additional inhibitor of one or more pro-inflammatory factors can be, without limitation, an antibody, an antigen-binding antibody fragment, an aptamer, an enzyme, a gene editing agent, an antibody mimetic, a small molecule, a nucleic acid, an organic or inorganic molecule, or a combination of any two or more thereof.

Particular TNF-α inhibitors include: infliximab, adalimumab, etanercept, golimumab, certrolizumab, TNF-related apoptosis-inducing ligand, thalidomide, pomalidomide, lenalidomide, apremilast, prednisone, efalizumab, ustekinumab, beclomethasone, betamethasone, cortisone, dexamethasone, hydrocortisone, methylprednisolone, prednisolone. In other aspects, TNF-α inhibitor may include one or more of infliximab, adalimumab, etanercept, golimumab, certrolizumab, TNF-related apoptosis-inducing ligand, thalidomide, pomalidomide, lenalidomide, apremilast, prednisone, efalizumab, and ustekinumab.

Particular IL-1β inhibitors include: anakinra, canakinumab, and rilonacept.

Particular IL-6 inhibitors include: tocilizumab, sarilumab, and satralizumab.

Particular IL-8 inhibitors include: BMS-986253 (abti-IL-8 mAb) and reparixin.

A particular IL-10 inhibitor is rituximab.

Particular ENA-78 inhibitors include LY294002 and SB225002

Particular RAGE inhibitors include azeliragon.
Particular MMP9 inhibitors include JNJ0966

Particular HER2 inhibitors include: trastuzumab, lapatinib, neratinib, margetuximab, pertuzumab, tucatinib, and dacomitinib.

Particular CXCR4 inhibitors include: periflaxor, AMD3100

AMD 11070 ( ).

Methods of Treatment

Methods of treatment of a subject having, or suspected of having, cancer, are provided which include administering an effective amount of a pharmaceutical composition according to aspects of the present disclosure to the subject.

The term "effective amount" as used herein refers to an amount needed to elicit the desired biological response in the subject being treated. In subjects having cancer or at risk for having cancer, an effective amount is effective to ameliorate one or more signs and/or symptoms of the condition.

The terms "subject" and "patient" are used interchangeably herein.

A subject treated according to methods and using compositions of the present disclosure can be mammalian or non-mammalian. A mammalian subject can be any mammal including, but not limited to, a human; a non-human primate; a rodent such as a mouse, rat, or guinea pig; a domesticated pet such as a cat or dog; a horse, cow, pig, sheep, goat, or rabbit. A non-mammalian subject can be any non-mammal including, but not limited to, a bird such as a duck, goose, chicken, or turkey.

A subject can be either gender and can be any age.

According to particular aspects, the subject is human. In certain aspects, the subject is a human male of African descent (AAM) or a human male of European descent (EAM).

According to particular aspects, the subject has cancer, or is suspected of having cancer. Cancers treated using methods and compositions described herein are characterized by abnormal cell proliferation including, but not limited to, pre-neoplastic hyperproliferation, cancer in-situ, neoplasms, and metastasis, and include solid and non-solid tumors. Examples of cancers treated according to aspects of the present disclosure include, but are not limited to, lymphoma, leukemia, squamous cell cancer, small-cell lung cancer, non-small cell lung cancer, adenocarcinoma of the lung, squamous carcinoma of the lung, cancer of the peritoneum, adrenal cancer, anal cancer, bile duct cancer, bladder cancer, brain cancer, breast cancer, triple negative breast cancer, central or peripheral nervous system cancers, cervical cancer, colon cancer, colorectal cancer, endometrial cancer, esophageal cancer, gall bladder cancer, gastrointestinal cancer, glioblastoma, head and neck cancer, kidney cancer, liver cancer, nasopharyngeal cancer, nasal cavity cancer, oropharyngeal cancer, oral cavity cancer, osteosarcoma, ovarian cancer, pancreatic cancer, parathyroid cancer, pituitary cancer, prostate cancer, retinoblastoma, sarcoma, salivary gland cancer, skin cancer, small intestine cancer, stomach cancer, testicular cancer, thymus cancer, thyroid cancer, uterine cancer, vaginal cancer and vulval cancer.

According to particular aspects, the subject has prostate cancer, or is suspected of having prostate cancer. According to particular aspects, the subject has prostate cancer, or is suspected of having castration resistant prostate cancer.

Methods and compositions of the present disclosure can be used for prophylaxis as well as amelioration of signs and/or symptoms of cancer. The terms "treating" and "treatment" used to refer to treatment of a cancer in a subject include: preventing, inhibiting or ameliorating the cancer in the subject, such as slowing progression of the cancer and/or reducing or ameliorating a sign or symptom of the cancer.

Methods and compositions of the present disclosure can be used for prophylaxis as well as amelioration of signs and/or symptoms of prostate cancer. The terms "treating" and "treatment" used to refer to treatment of a prostate cancer in a subject include: preventing, inhibiting or ameliorating the prostate cancer in the subject, such as slowing progression of the prostate cancer and/or reducing or ameliorating a sign or symptom of the prostate cancer.

According to aspects, a subject is an individual in need of diagnosis based on particular symptoms or family history.

Methods of the present disclosure include further include administering an additional therapeutic agent to the subject.

Methods of the present disclosure include further include administering an additional therapeutic agent to the subject, wherein the additional therapeutic agent comprises an additional inhibitor of a proinflammatory cytokine or chemokine.

The additional inhibitor can be a nucleic acid inhibitor, an antibody, an antigen-binding antibody fragment, an aptamer, an inorganic or organic small molecule inhibitor, or a combination of any two or more thereof.

Methods of the present disclosure include further include administering an additional therapeutic agent which is or includes an anti-cancer agent.

Adjunct Treatment

According to aspects of the present disclosure, a method of treating a subject having, or suspected of having, cancer further includes an adjunct anti-cancer treatment. An adjunct anti-cancer treatment can be a radiation treatment of a subject or an affected area of a subject's body.

An adjunct anti-cancer treatment for prostate cancer can be a chemical or surgical castration, for example.

An additional therapeutic treatment or adjunct anti-cancer treatment for prostate cancer can include, without limitation, cryotherapy, external beam radiotherapy, hormonal therapy, interstitial prostate brachytherapy, radical prostatectomy and pharmaceutical therapies such as, but not limited to, administration of an anticholinergic agent; administration of an alpha-1-adrenergic receptor antagonist (also called alpha blockers), illustratively including alfuzosin, doxazosin, silodosin, tamsulosin, and terazosin; administration of a 5-alpha-reductase inhibitor, illustratively including dutasteride and finasteride; or a combination of two or more of an alpha-blocker, a 5-alpha-reductase inhibitor and an anticholinergic agent.

Administration

According to aspects of the present disclosure, a combination including or consisting of a compound of the present disclosure, and/or a salt, derivative, and/or isomer thereof, and one or more additional therapeutic agents is included in a pharmaceutical composition administered to a subject in need thereof. A combination including or consisting of a compound of the present disclosure, and/or a salt, derivative, and/or isomer thereof, and one or more additional therapeutic agents may be administered separately in separate formulations, or together.

Methods of the present disclosure include local administration of a pharmaceutical composition including a combination including or consisting of a compound of the present disclosure, and/or a salt, derivative, and/or isomer thereof, of the present disclosure.

Methods of the present disclosure include intratumoral administration of a pharmaceutical composition including a combination including or consisting of a compound of the present disclosure, and/or a salt, derivative, and/or isomer thereof.

Methods of the present disclosure include administration of a pharmaceutical composition including a combination including or consisting of a compound of the present disclosure, and/or a salt, derivative, and/or isomer thereof, by a route of administration including, but not limited to, oral, rectal, nasal, pulmonary, epidural, ocular, otic, intraarterial, intracardiac, intracerebroventricular, intradermal, intravenous, intramuscular, intraperitoneal, intraosseous, intrapulmonary, intrathecal, intratumoral, intravesical, ophthalmic, parenteral, subcutaneous, topical, transdermal, and transmucosal, such as by sublingual, buccal, vaginal, and inhalational, routes of administration.

Methods of the present disclosure include administration of a pharmaceutical composition including a combination including or consisting of a compound of the present disclosure, and/or a salt, derivative, and/or isomer thereof, by direct administration to the prostate and/or a prostate tumor.

The dosage of a combination including or consisting of a compound of the present disclosure, and/or a salt, derivative, and/or isomer thereof, and any optional additional therapeutic agent will vary based on factors such as, but not limited to, the route of administration; the age, health, sex, and weight of the subject to whom the pharmaceutical composition is to be administered; the nature and extent of the subject's symptoms, if any, and the effect desired. Dosage may be adjusted depending on whether treatment is to be acute or continuing. One of skill in the art can determine a pharmaceutically effective amount in view of these and other considerations typical in medical practice.

Assays

According to particular aspects of the present disclosure, a subject to be treated is characterized by one or more dysregulated pro-inflammatory factors in the subject, wherein the one or more dysregulated pro-inflammatory factors includes one or more of: a dysregulated pro-inflammatory cytokine, a dysregulated pro-inflammatory chemokine, a dysregulated pro-inflammatory cytokine receptor, a dysregulated pro-inflammatory chemokine receptor, or a dysregulated stimulator of any of these.

According to aspects of the present disclosure the one or more dysregulated pro-inflammatory factors is CXCR4, and one or more of: TNF-alpha, IL-1beta, IL-6, and IL-8.

According to aspects of the present disclosure the one or more dysregulated pro-inflammatory factors in the subject to be treated is CXCR4, and one or more of: TNF-alpha, IL-1beta, IL-6, and IL-8; and further includes one or more additional dysregulated pro-inflammatory factors selected from the group consisting of: interleukin-10 (IL-10), stromal cell-derived factor-1α (SDF-1α, also known as C—X—C motif chemokine ligand 12 (CXCL12)), matrix metallopeptidase 9 (MMP-9)), epithelial-derived neutrophil-activating peptide 78 (ENA-78, also known as C—X—C motif chemokine ligand 5 (CXCL5)), receptor for advanced glycation end products (RAGE), HER2 (human epidermal growth factor receptor 2, also known as receptor tyrosine-protein kinase erbB2 or CD340), and leptin.

Cancers treated using methods and compositions according to aspects of the present disclosure are characterized by abnormal cell proliferation and a dysregulated cytokine, a dysregulated chemokine, a dysregulated cytokine receptor, a dysregulated chemokine receptor, a dysregulated stimulator of any of the forgoing, or a combination of any two or more thereof.

Cancers treated using methods and compositions according to aspects of the present disclosure are characterized by abnormal cell proliferation and a dysregulated pro-inflammatory factor which is CXCR4, and one or more of: TNF-alpha, IL-1beta, IL-6, and IL-8; and may further include one or more additional dysregulated pro-inflammatory factors selected from the group consisting of: interleukin-10 (IL-10), stromal cell-derived factor-1α (SDF-1α, also known as C—X—C motif chemokine ligand 12 (CXCL12)), matrix metallopeptidase 9 (MMP-9)), epithelial-derived neutrophil-activating peptide 78 (ENA-78, also known as C—X—C motif chemokine ligand 5 (CXCL5)), receptor for advanced glycation end products (RAGE), HER2 (human epidermal growth factor receptor 2, also known as receptor tyrosine-protein kinase erbB2 or CD340), and leptin.

According to particular aspects, the subject has prostate cancer, or is suspected of having prostate cancer, including pre-neoplastic hyperproliferation, cancer in-situ, neoplasms, and metastasis, and include solid and non-solid tumors. Prostate cancers treated using methods and compositions according to aspects of the present disclosure are characterized by abnormal cell proliferation and a dysregulated pro-inflammatory factor which is a dysregulated cytokine, a dysregulated chemokine, a dysregulated cytokine receptor, a dysregulated chemokine receptor, a dysregulated stimulator of any of the foregoing, or any two or more thereof.

Prostate cancers treated using methods and compositions according to aspects of the present disclosure are characterized by abnormal cell proliferation, and a dysregulated pro-inflammatory factor which is CXCR4, and one or more of: TNF-alpha, IL-1beta, IL-6, and IL-8; and may further include one or more additional dysregulated pro-inflammatory factors selected from the group consisting of: interleukin-10 (IL-10), stromal cell-derived factor-1α (SDF-1α, also known as C—X—C motif chemokine ligand 12 (CXCL12)), matrix metallopeptidase 9 (MMP-9)), epithelial-derived neutrophil-activating peptide 78 (ENA-78, also known as C—X—C motif chemokine ligand 5 (CXCL5)), receptor for advanced glycation end products (RAGE), HER2 (human epidermal growth factor receptor 2, also known as receptor tyrosine-protein kinase erbB2 or CD340), and leptin.

The term "dysregulated" as used herein to refer to a pro-inflammatory factor, particularly a pro-inflammatory cytokine, pro-inflammatory chemokine, pro-inflammatory cytokine receptor, pro-inflammatory chemokine receptor, or stimulator of any of the foregoing, indicates that the expression, level, activity, localization, or other characteristic of the cytokine, chemokine, cytokine receptor, or chemokine receptor, is abnormal in a subject sample compared to a control.

According to particular aspects of the present disclosure, a pro-inflammatory factor, particularly a pro-inflammatory cytokine, pro-inflammatory chemokine, pro-inflammatory cytokine receptor, pro-inflammatory chemokine receptor, or stimulator of any of the foregoing, is determined to be dysregulated in a subject having cancer or suspected of having cancer, by an assay to assess the expression, level, activity, localization, or other characteristic of one or more of: a pro-inflammatory cytokine, pro-inflammatory chemokine, pro-inflammatory cytokine receptor, pro-inflammatory chemokine receptor, or stimulator of any of the foregoing, in a subject sample.

According to particular aspects of the present disclosure, a pro-inflammatory factor, particularly a pro-inflammatory cytokine, pro-inflammatory chemokine, pro-inflammatory cytokine receptor, pro-inflammatory chemokine receptor, or stimulator of any of the foregoing, is determined to be dysregulated in a subject having cancer, or suspected of having cancer, by an assay to assess the expression, level, activity, localization, or other characteristic of CXCR4, and one or more of: TNF-alpha, IL-1beta, IL-6, and IL-8; and may further include one or more additional dysregulated pro-inflammatory factors selected from the group consisting of: interleukin-10 (IL-10), stromal cell-derived factor-1α (SDF-1α, also known as C—X—C motif chemokine ligand 12 (CXCL12)), matrix metallopeptidase 9 (MMP-9)), epithelial-derived neutrophil-activating peptide 78 (ENA-78, also known as C—X—C motif chemokine ligand 5 (CXCL5)), receptor for advanced glycation end products (RAGE), HER2 (human epidermal growth factor receptor 2, also known as receptor tyrosine-protein kinase erbB2 or CD340), and leptin.

According to particular aspects of the present disclosure, a pro-inflammatory factor, particularly a pro-inflammatory cytokine, pro-inflammatory chemokine, pro-inflammatory cytokine receptor, pro-inflammatory chemokine receptor, or stimulator of any of the foregoing, is determined to be dysregulated in a subject having prostate cancer or suspected of having prostate cancer, by an assay to assess the expression, level, activity, localization, or other characteristic of a pro-inflammatory factor, particularly a pro-inflammatory cytokine, pro-inflammatory chemokine, pro-inflammatory cytokine receptor, pro-inflammatory chemokine receptor, or stimulator of any of the foregoing, in a subject sample.

According to particular aspects of the present disclosure, a pro-inflammatory factor, particularly a pro-inflammatory cytokine, pro-inflammatory chemokine, pro-inflammatory cytokine receptor, pro-inflammatory chemokine receptor, or stimulator of any of the foregoing, is determined to be dysregulated in a subject having prostate cancer, or suspected of having prostate cancer, by an assay to assess the expression, level, activity, localization, or other characteristic of CXCR4, and one or more of: TNF-alpha, IL-1beta, IL-6, and IL-8; and may further include one or more additional dysregulated pro-inflammatory factors selected from the group consisting of: interleukin-10 (IL-10), stromal cell-derived factor-1α (SDF-1α, also known as C—X—C motif chemokine ligand 12 (CXCL12)), matrix metallopeptidase 9 (MMP-9)), epithelial-derived neutrophil-activating peptide 78 (ENA-78, also known as C—X—C motif chemokine ligand 5 (CXCL5)), receptor for advanced glycation end products (RAGE), HER2 (human epidermal growth factor receptor 2, also known as receptor tyrosine-protein kinase erbB2 or CD340), and leptin.

Methods of the present disclosure include assaying one or more of: CXCR4, TNF, IL-1beta, IL-6, and IL-8 in a subject sample.

Methods of the present disclosure include assaying one or more of: CXCR4, TNF, IL-1beta, IL-6, and IL-8 in a subject sample obtained from the subject prior to administering an effective amount of the pharmaceutical composition to the subject.

Methods of the present disclosure include assaying one or more of: CXCR4, TNF, IL-1beta, IL-6, and IL-8 in a subject sample obtained from the subject after administering an effective amount of the pharmaceutical composition to the subject.

Methods of the present disclosure include assaying one or more of: CXCR4, TNF, IL-1beta, IL-6, and IL-8 in a subject sample obtained from the subject before and after administering an effective amount of the pharmaceutical composition to the subject.

The term "subject sample" as used herein refers to any material, including, without limitation, a biological fluid, cell or tissue, obtained from, or derived from, a subject that contains, or is suspected of containing, the substance to be assayed, illustratively including blood, plasma, serum, urine, saliva, ascites, cerebrospinal fluid, cerebroventricular fluid, pleural fluids, pulmonary and bronchial lavage samples, mucous, sweat, tears, semen, bladder wash samples, amniotic fluid, lymph, peritoneal fluid, synovial fluid, bone marrow aspirate, tumor cells or tissue, organ cells or tissue, such as biopsy material. According to aspects of the present disclosure, a subject sample includes cultured cells or cultured tissues. According to aspects of the present disclosure, a subject sample includes cells or tissues implanted in an animal of a different species, such as human cells or tissues implanted in a mouse.

According to aspects of the present disclosure, a "subject sample" is a blood sample obtained from a subject having, or suspected of having prostate cancer. According to aspects of the present disclosure, a "subject sample" is a plasma sample obtained from a subject having, or suspected of having prostate cancer. According to aspects of the present disclosure, a "subject sample" is a prostate tissue sample obtained from a subject having, or suspected of having prostate cancer. According to aspects of the present disclosure, a "subject sample" is a semen or urine sample obtained from a subject having, or suspected of having prostate cancer.

An assay to assess dysregulation of one or more of: a pro-inflammatory factor, particularly a pro-inflammatory cytokine, pro-inflammatory chemokine, pro-inflammatory cytokine receptor, pro-inflammatory chemokine receptor, or stimulator of any of the foregoing, in a subject sample, are performed using techniques such as nucleic acid assays, spectrometric assays, immunoassays, and functional assays. A mutation status of one or more of: a pro-inflammatory factor, particularly a pro-inflammatory cytokine, pro-inflammatory chemokine, pro-inflammatory cytokine receptor, pro-inflammatory chemokine receptor, or stimulator of any of the foregoing, in a subject sample, can be assessed using assays such as protein or peptide sequencing, nucleic acid assay and immunoassay.

Nucleic acid assays for assessing nucleic acids encoding a pro-inflammatory factor, particularly a pro-inflammatory cytokine, pro-inflammatory chemokine, pro-inflammatory cytokine receptor, pro-inflammatory chemokine receptor, or stimulator of any of the foregoing, particularly mRNA or cDNA, in a subject sample, include, but are not limited to, sequencing; polymerase chain reactions (PCR) such as RT-PCR; dot blot; in situ hybridization; Northern blot; RNase protection; RNase protection assay; microarray analysis; and cDNA-mediated Annealing, Selection, extension, and Ligation (DASL) assay (Chow et al., Front Genet. 2012, 3:11). Nucleic acid assays are described in detail, for example, in Sambrook, J. and Russell, D. W., Molecular Cloning: A Laboratory Manual, Cold Spring Harbor Laboratory Press, 3rd Ed, 2001; and F. M. Ausubel, Ed., Short Protocols in Molecular Biology, Current Protocols, 5th Ed., 2002.

Immunoassays can be used to assess a pro-inflammatory factor, particularly a pro-inflammatory cytokine, pro-inflammatory chemokine, pro-inflammatory cytokine receptor, pro-inflammatory chemokine receptor, or stimulator of any of the foregoing, in a subject sample, including, but not limited to, enzyme-linked immunosorbent assay (ELISA), enzyme-linked immunofiltration assay (ELIFA), flow cytometry, immunoblot, immunoprecipitation, immunohistochemistry, immunocytochemistry, luminescent immunoassay (LIA), fluorescent immunoassay (FIA), and radioimmunoassay. Immunoassays are described in detail, for example, in Harlow, E. and Lane, D., Antibodies: A Laboratory Manual, Cold Spring Harbor Laboratory Press, 1988; Ausubel. F. et al., (Eds.), Short Protocols in Molecular Biology, Wiley, 2002; and J. D. Pound (Ed.) Immunochemical Protocols, Methods in Molecular Biology, Humana Press, 2nd ed., 1998; B. K. C. Lo (Ed.).

Functional assays can be used to assess a pro-inflammatory factor, particularly a pro-inflammatory cytokine, pro-inflammatory chemokine, pro-inflammatory cytokine receptor, pro-inflammatory chemokine receptor, or stimulator of any of the foregoing, in a subject sample, including, but not limited to, assessing activity of the cytokine, the chemokine, the cytokine receptor, or the chemokine receptor to bind to a binding partner, such as a ligand or receptor.

Spectrometric analysis can be used to assay a sample for one or more pro-inflammatory factors of the present disclosure. Any of various spectroscopy methods can be used to assay one or more pro-inflammatory factors and/or one or more biomarkers of the present disclosure, including, but not limited to, gas chromatography, liquid chromatography, ion mobility spectrometry, mass spectrometry, liquid chromatography-mass spectrometry (LC-MS or HPLC-MS), ion mobility spectrometry-mass spectrometry, tandem mass spectrometry, gas chromatography-mass spectrometry, matrix-assisted desorption ionization time-of-flight (MALDI-TOF) mass spectrometry, surface-enhanced laser desorption ionization (SELDI) and nuclear magnetic resonance spectroscopy, all of which are well-known to the skill artisan.

For example, mass analysis can be used in an assay according to aspects of the present disclosure. Mass analysis is conducted using, for example, time-of-flight (TOF) mass spectrometry or Fourier transform ion cyclotron resonance mass spectrometry. Mass spectrometry techniques are known in the art and exemplary detailed descriptions of methods for protein and/or peptide assay are found in Li J., et al., Clin Chem., 48(8):1296-304, 2002; Hortin, G. L., Clinical Chemistry 52: 1223-1237, 2006; Hortin, G. L., Clinical Chemistry 52: 1223-1237, 2006; A. L. Burlingame, et al. (Eds.), Mass Spectrometry in Biology and Medicine, Humana Press, 2000; and D. M. Desiderio, Mass Spectrometry of Peptides, CRC Press, 1990.

Assays according to aspects of the present disclosure can be multiplex, i.e. assays for two or more pro-inflammatory factors.

One or more standards and/or controls can be used to allow assessment, including quantitative assessment, of gene, biomarker, and/or a pro-inflammatory factor.

One or more standards and/or controls can be used to allow assessment, of dysregulation of a pro-inflammatory factor, particularly a pro-inflammatory cytokine, pro-inflammatory chemokine, pro-inflammatory cytokine receptor, pro-inflammatory chemokine receptor, or stimulator of any of the foregoing, in a subject sample.

According to aspects of the present disclosure, assaying a pro-inflammatory factor, particularly a pro-inflammatory cytokine, pro-inflammatory chemokine, pro-inflammatory cytokine receptor, pro-inflammatory chemokine receptor, or stimulator of any of the foregoing, to detect dysregulation thereof includes use of a control, also referred to interchangeably as a "suitable control," an "appropriate control," a "control sample," or a "reference." Thus, assays according to aspects of the present disclosure may include a step that involves comparing a detected aspect, such as level, activity, localization, or other characteristic, to a suitable control. A control is any control or standard useful for comparison purposes to detect dysregulation of a pro-inflammatory factor, particularly a pro-inflammatory cytokine, pro-inflammatory chemokine, pro-inflammatory cytokine receptor, pro-inflammatory chemokine receptor, or stimulator of any of the foregoing, in a subject sample from a subject having or suspected of having cancer. In some aspects, a control is a level, activity, localization, expression characteristic, or other characteristic of a pro-inflammatory factor, particularly a pro-inflammatory cytokine, pro-inflammatory chemokine, pro-inflammatory cytokine receptor, pro-inflammatory chemokine receptor, or stimulator of any of the foregoing, determined in a subject, or population of, "normal" subjects. A control can be a reference value previously determined and stored in a print or electronic medium for recall and comparison.

In other aspects, a control is a detected aspect, such as expression, level, activity, localization, or other characteristic, of a pro-inflammatory factor, particularly a pro-inflammatory cytokine, pro-inflammatory chemokine, pro-inflammatory cytokine receptor, pro-inflammatory chemokine receptor, or stimulator of any of the foregoing, determined prior to treating the subject having, or suspected of having, cancer, which is compared to a detected aspect, such as expression, level, activity, localization, or other characteristic, of a pro-inflammatory factor, particularly a pro-inflammatory cytokine, pro-inflammatory chemokine, pro-inflammatory cytokine receptor, pro-inflammatory chemokine receptor, or stimulator of any of the foregoing, determined during or after treating the subject.

A control can be a profile or pattern of one or more aspects detected by an assay, such as expression, level, activity, localization, or other characteristic, of one or more pro-inflammatory factors which can be compared with a profile or pattern of one or more aspects determined in a subject sample.

A control can be an amount of one or more pro-inflammatory factors of the present disclosure present in a comparable sample obtained from the same subject at a different time. For example, a standard can be an amount of one or more pro-inflammatory factors of the present disclosure present in a comparable sample obtained from the same subject at an earlier time. A first sample can be obtained from an individual subject at a first time to obtain a subject-specific baseline level of the one or more pro-inflammatory factors of the present disclosure in the first sample. A second sample can be obtained from the individual subject at a second time and assayed for one or more pro-inflammatory factors of the present disclosure to monitor differences in the levels of the one or more pro-inflammatory factors of the present disclosure compared to the first sample, thereby monitoring health and/or disease in the subject. Additional samples can be obtained from the subject at additional time points and assayed for pro-inflammatory factors to monitor differences in the levels of the corresponding one or more pro-inflammatory factors of the present disclosure compared to the first sample, second sample or other samples, thereby monitoring health and/or disease in the subject.

A standard can be an average level of one or more pro-inflammatory factors of the present disclosure present in comparable samples of one or more populations. The "average level" is determined by assay of the one or more pro-inflammatory factors of the present disclosure in comparable samples obtained from each member of the population. The term "comparable sample" is used to indicate that the samples are of the same type. For example, each of the comparable samples is a plasma sample. In a further example, each of the comparable samples is a biopsy sample.

A difference detected in levels of one or more pro-inflammatory factors of the present disclosure compared to a standard can be an increase or decrease in level of the one or more pro-inflammatory factors. A difference detected in levels of one or more pro-inflammatory factors of the present disclosure compared to a standard can be a detectable level of the one or more pro-inflammatory factors where the pro-inflammatory factor is undetectable in the standard. A difference detected in levels of one or more pro-inflammatory factors of the present disclosure compared to a standard can be an undetectable level of the one or more pro-inflammatory factors where the biomarker is detectable in the standard.

Assay results can be analyzed using statistical analysis by any of various methods, exemplified by parametric or non-parametric tests, analysis of variance, analysis of covariance, logistic regression for multivariate analysis, Fisher's exact test, the chi-square test, Student's T-test, the Mann-Whitney test, Wilcoxon signed ranks test, McNemar test, Friedman test and Page's L trend test. These and other statistical tests are well-known in the art as detailed in Hicks, C M, Research Methods for Clinical Therapists: Applied Project Design and Analysis, Churchill Livingstone; 5th Ed., 2009; and Freund, R J et al., Statistical Methods, Academic Press; 3rd Ed., 2010.

Embodiments of inventive compositions and methods are illustrated in the following examples. These examples are provided for illustrative purposes and are not considered limitations on the scope of inventive compositions and methods.

EXAMPLES

An exemplary synthetic scheme for a compound having structural formula (II) is shown in FIG. 2.

Preparation of compound 2: To a solution of methyl 2,4-dihydroxybenzoate 1 in $Et_2O$ at room temperature is added sulfuryl chloride. The mixture is heated under reflux for 18 hours. Additional amount of sulfuryl chloride is added as necessary to give 2.

Preparation of compound 4: To a mixture of 2 and 3 in THF at room temperature is added triphenylphosphine. A solution of diisopropylazodicarboxylate (DIAD) in THF is then added dropwise via addition funnel (approximately 1 drop/3 seconds). The reaction mixture is stirred at room temperature for 15-20 hours to afford 4.

Preparation of compound 5: To a solution of compound 4 in mixture of $THF:EtOH:H_2O$ (4:2:1) solvents at room temperature is added 10N LiOH. The reaction mixture is stirred at room temperature for 18 hours to afford compound 5.

Preparation of 7: To a solution of 5 and DIPEA in DMF at room temperature is added HATU. The reaction mixture is then stirred at room temperature for 30 min. intermediate 6 is then added and the reaction mixture was stirred at room temperature for 24 hours to give 7.

Preparation of 10: To a solution of (R/S)-5,6,7,8-Tetrahydroquinolin-8-amine (8) in DCM is added intermediate 9. Then, sodium triacetoxyborohydride is added to the solution and the mixture is stirred at room temperature for 18 hours to give 10.

Preparation of 12: To a mixture of 10 and 11 in acetonitrile at room temperature is added KI and DIPEA. The mixture is then refluxed at 70° C. to afford compound 12.

Preparation of 13: Compound 12 is treated with HCl/AcOH. The resulting mixture is stirred at room temperature to give 13.

Preparation of 14: To the mixture of 13 in DMF at room temperature is added $K_2CO_3$ then compound 7 is added and the reaction mixture is stirred at room temperature for 18 hours to afford the target compound 14.

Items

Item 1. A compound comprising structural formula (I):

where X is O, NH, or S; where $R_1$, $R_2$, and $R_3$, are each independently selected from the group consisting of H, Br, F, methyl, Cl, OH, CN, $NH_2$, and $CF_3$; where $R_4$ is H, $C_1$-$C_6$ unsubstituted or substituted, alkyl, cycloalkyl, aryl, phenyl, heteroalkyl, heterocycloalkyl, or heteroaryl; where $R_5$ is COOH, $CO_2R$, $SO_3H$, $SO_2NH_2$, $PO_3H$, $CONH_2$, CONHOH, and $SO_2NHR$ where R is methyl, ethyl, $CF_3$, $CHF_2$, or $CHF_3$; where HetAr is benzamidazolyl, benzoxazolyl, imidazopyridinyl, or imidazopyramidinyl; and where $n_1$ is 0-2, $n_2$ is 0-5, and $n_3$ is 0-3; or an isomer, salt, or derivative thereof.

Item 2. The compound of item 1, comprising structural formula (I):

where X is O, NH, or S; where $R_1$, $R_2$, and $R_3$, are each independently selected from the group consisting of H, Br, F, methyl, Cl, OH, CN, $NH_2$, and $CF_3$; where $R_4$ is H, methyl, isopropyl, phenyl, ethyl, cyclopropyl, cyclohexyl, or methylcyclohexyl; where $R_5$ is COOH, $CO_2R$, $SO_3H$, $SO_2NH_2$, $PO_3H$, $CONH_2$, CONHOH, and $SO_2NHR$ where R is methyl, ethyl, $CF_3$, $CHF_2$, or $CHF_3$; where HetAr is benzamidazolyl, benzoxazolyl, imidazopyridinyl, or imidazopyramidinyl; and where $n_1$ is 0-2, $n_2$ is 0-5, and $n_3$ is 0-3; or an isomer, salt, or derivative thereof.

Item 3. The compound of item 1, comprising the structural formula (II):

or an isomer, salt, or derivative thereof.

Item 4. The compound of item 1, 2, or 3, wherein the salt is a pharmaceutically acceptable salt.

Item 5. The compound of any of items 1 to 4, wherein the derivative is an ester, amide, or hydrate.

Item 6. A pharmaceutical composition, comprising: a compound according to any of items 1 to 5; and a pharmaceutically acceptable carrier.

Item 7. The compound or pharmaceutical composition according to any of items 1 to 6, wherein the compound is an inhibitor of CXCR4 and one or more of: TNF, IL-1beta, IL-6, and IL-8.

Item 8. A method of treatment of a subject having, or suspected of having, cancer, comprising: administering an effective amount of a pharmaceutical composition according to item 6 or 7 to the subject.

Item 9. The method of treatment of item 8, wherein the administering comprises systemic administration.

Item 10. The method of treatment of item 8 or 9, wherein the administering comprises local administration.

Item 11. The method of treatment of any of items 8 to 10, further comprising assaying one or more of: CXCR4, TNF, IL-1beta, IL-6, and IL-8 in a subject sample.

Item 12. The method of treatment of any of items 8 to 11, further comprising assaying one or more of: CXCR4, TNF, IL-1beta, IL-6, and IL-8 in a subject sample obtained from the subject prior to administering the effective amount of the pharmaceutical composition.

Item 13. The method of treatment of any of items 8 to 12, further comprising assaying one or more of: CXCR4, TNF, IL-1beta, IL-6, and IL-8 in a subject sample obtained from the subject after administering the effective amount of the pharmaceutical composition.

Item 14. The method of treatment of any of items 8 to 13, further comprising administering an additional therapeutic agent to the subject.

Item 15. The method of treatment of item 14, wherein the additional therapeutic agent comprises an additional inhibitor of a proinflammatory cytokine or chemokine.

Item 16. The method of treatment of item 15, wherein the additional inhibitor comprises a nucleic acid inhibitor, an antibody, an antigen-binding antibody fragment, an aptamer, an inorganic or organic small molecule inhibitor, or a combination of any two or more thereof.

Item 17. The method of treatment of any of items 14 to 16, wherein the additional therapeutic agent comprises an anticancer agent.

Item 18. The method of treatment of any of items 8 to 17, further comprising administering an adjunct anti-cancer treatment to the subject.

Item 19. The method of treatment of item 18, wherein the adjunct anti-cancer therapy comprises surgery and/or radiation treatment.

Item 20. The method of treatment of any of items 8 to 19, wherein the cancer is prostate cancer.

Item 21. The method of treatment of any of items 8 to 20, wherein the prostate cancer is castration resistant prostate cancer.

Any patents or publications mentioned in this specification are incorporated herein by reference to the same extent as if each individual publication is specifically and individually indicated to be incorporated by reference.

The compositions and methods described herein are presently representative of preferred embodiments, exemplary, and not intended as limitations on the scope of the invention. Changes therein and other uses will occur to those skilled in the art. Such changes and other uses can be made without departing from the scope of the invention as set forth in the claims.

The invention claimed is:

1. A compound comprising structural formula (I):

where X is O, NH, or S; where $R_1$, $R_2$, and $R_3$, are each independently selected from the group consisting of H, Br, F, methyl, Cl, OH, CN, $NH_2$, and $CF_3$; where $R_4$ is H, $C_1$-$C_6$ unsubstituted or substituted alkyl, cycloalkyl, aryl, phenyl, heteroalkyl, heterocycloalkyl, or heteroaryl; where $R_5$ is COOH, $CO_2R$, $SO_3H$, $SO_2NH_2$, $PO_3H$, $CONH_2$, CONHOH, or $SO_2NHR$ where R is methyl, ethyl, $CF_3$, $CHF_2$, or $CHF_3$; where HetAr is benzamidazolyl, benzoxazolyl, imidazopyridinyl, or imidazopyramidinyl; and where $n_1$ is 0-2, $n_2$ is 0-5, and $n_3$ is 0-3; or a salt thereof.

2. The compound of claim 1, comprising structural formula (I):

where X is O, NH, or S; where $R_1$, $R_2$, and $R_3$, are each independently selected from the group consisting of H, Br, F, methyl, Cl, OH, CN, $NH_2$, and $CF_3$; where $R_4$ is H, methyl, isopropyl, phenyl, ethyl, cyclopropyl, cyclohexyl, or methylcyclohexyl; where $R_5$ is COOH, $CO_2R$, $SO_3H$, $SO_2NH_2$, $PO_3H$, $CONH_2$, CONHOH, or $SO_2NHR$ where R is methyl, ethyl, $CF_3$, $CHF_2$, or $CHF_3$; where HetAr is benzamidazolyl, benzoxazolyl, imidazopyridinyl, or imidazopyramidinyl; and where $n_1$ is 0-2, $n_2$ is 0-5, and $n_3$ is 0-3; or a salt thereof.

3. The compound of claim 1, comprising the structural formula (II):

or a salt thereof.

4. The compound of claim 1, wherein the salt is a pharmaceutically acceptable salt.

5. A pharmaceutical composition, comprising: the compound according to claim 1; and a pharmaceutically acceptable carrier.

6. The compound according to claim 1, wherein the compound is an inhibitor of CXCR4 and one or more of: TNF, IL-1beta, IL-6, and IL-8.

7. A method of treatment of a subject having, or suspected of having, cancer, comprising:
administering an effective amount of the pharmaceutical composition according to claim 5 to the subject.

8. The method of treatment of claim 7, wherein the administering comprises systemic administration.

9. The method of treatment of claim 7, wherein the administering comprises local administration.

10. The method of treatment of claim 7, further comprising assaying one or more of: CXCR4, TNF, IL-1beta, IL-6, and IL-8 in a subject sample.

11. The method of treatment of claim 7, further comprising assaying one or more of: CXCR4, TNF, IL-1beta, IL-6, and IL-8 in a subject sample obtained from the subject prior to administering the effective amount of the pharmaceutical composition.

12. The method of treatment of claim 7, further comprising assaying one or more of: CXCR4, TNF, IL-1beta, IL-6, and IL-8 in a subject sample obtained from the subject after administering the effective amount of the pharmaceutical composition.

13. The method of treatment of claim 7, further comprising administering an additional therapeutic agent to the subject.

14. The method of treatment of claim 13, wherein the additional therapeutic agent comprises an additional inhibitor of a proinflammatory cytokine or chemokine.

15. The method of treatment of claim 14, wherein the additional inhibitor comprises a nucleic acid inhibitor, an antibody, an antigen-binding antibody fragment, an aptamer, an inorganic or organic small molecule inhibitor, or a combination of any two or more thereof.

16. The method of treatment of claim 13, wherein the additional therapeutic agent comprises an anti-cancer agent.

17. The method of treatment of claim 7, further comprising administering an adjunct anti-cancer treatment to the subject.

18. The method of treatment of claim 17, wherein the adjunct anti-cancer therapy comprises surgery and/or radiation treatment.

19. The method of treatment of claim 7, wherein the cancer is prostate cancer.

20. The method of treatment of claim 19, wherein the prostate cancer is castration resistant prostate cancer.

* * * * *